United States Patent
Tashiro

(10) Patent No.: US 9,289,186 B2
(45) Date of Patent: Mar. 22, 2016

(54) ULTRASOUND DIAGNOSTIC APPARATUS

(71) Applicant: FUJIFILM Corporation, Tokyo (JP)

(72) Inventor: Rika Tashiro, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 98 days.

(21) Appl. No.: 13/846,719

(22) Filed: Mar. 18, 2013

(65) Prior Publication Data

US 2013/0261447 A1 Oct. 3, 2013

(30) Foreign Application Priority Data

Apr. 2, 2012 (JP) ................................. 2012-083768

(51) Int. Cl.
*A61B 8/00* (2006.01)
*A61B 8/08* (2006.01)

(52) U.S. Cl.
CPC . *A61B 8/44* (2013.01); *A61B 8/465* (2013.01); *A61B 8/467* (2013.01); *A61B 8/5223* (2013.01); *A61B 8/0866* (2013.01); *A61B 8/4427* (2013.01); *A61B 8/461* (2013.01)

(58) Field of Classification Search
CPC . G01S 7/52053; G01S 7/52074; A61B 8/467; A61B 8/14; A61B 8/44; A61B 8/0866; A61B 8/4427; A61B 8/465; A61B 8/5223; A61B 8/461; G01N 29/0609; G01N 29/0618; G01N 29/0645; G01N 29/0654; G06F 19/321; G06T 2207/10132
USPC ............................ 600/437–469; 382/128–132
See application file for complete search history.

(56) References Cited

U.S. PATENT DOCUMENTS

| | | | | |
|---|---|---|---|---|
| 5,161,535 A | * | 11/1992 | Short et al. ..................... | 600/437 |
| 5,315,999 A | * | 5/1994 | Kinicki et al. ................ | 600/443 |
| 2003/0135116 A1 | | 7/2003 | Ogasawara et al. | |
| 2004/0179332 A1 | | 9/2004 | Smith et al. | |
| 2006/0270938 A1 | | 11/2006 | Yawata | |
| 2008/0267499 A1 | * | 10/2008 | Deischinger et al. ......... | 382/173 |
| 2010/0094100 A1 | | 4/2010 | Fujii et al. | |
| 2010/0305444 A1 | * | 12/2010 | Fujii et al. ..................... | 600/443 |
| 2010/0312113 A1 | * | 12/2010 | Ogasawara et al. ........... | 600/443 |
| 2011/0178405 A1 | * | 7/2011 | Chono .......................... | 600/443 |
| 2011/0263980 A1 | * | 10/2011 | Mills et al. .................... | 600/439 |

(Continued)

FOREIGN PATENT DOCUMENTS

| | | |
|---|---|---|
| JP | 2001-137237 A | 5/2001 |
| JP | 2003-153903 A | 5/2003 |

(Continued)

OTHER PUBLICATIONS

United States Office Action dated Jul. 7, 2015 in co-pending U.S. Appl. No. 14/034,809.

(Continued)

*Primary Examiner* — Sanjay Cattungal
(74) *Attorney, Agent, or Firm* — McGinn IP Law Group, PLLC

(57) ABSTRACT

An ultrasound diagnostic apparatus includes a monitor simultaneously displaying in blocks a series of examination items on an ultrasound diagnosis within a screen in chronological order and a controller causing the monitor to highlight a block of an examination item being currently executed among blocks indicating the series of examination items displayed on the monitor.

10 Claims, 6 Drawing Sheets

(56) References Cited

U.S. PATENT DOCUMENTS

| | | | |
|---|---|---|---|
| 2012/0014578 A1* | 1/2012 | Karssemeijer et al. | 382/131 |
| 2012/0262460 A1 | 10/2012 | Endo et al. | |
| 2013/0261447 A1 | 10/2013 | Tashiro | |
| 2014/0309530 A1 | 10/2014 | Chono | |
| 2015/0057541 A1* | 2/2015 | Yang et al. | 600/437 |

FOREIGN PATENT DOCUMENTS

| | | | |
|---|---|---|---|
| JP | 2005-270424 A | 10/2005 | |
| JP | 2006-271862 A | 10/2006 | |
| JP | 2006-333896 A | 12/2006 | |
| JP | 2007-029456 A | 2/2007 | |
| JP | 2010-115478 A | 5/2010 | |
| JP | 2011-010689 A | 1/2011 | |
| WO | WO 2011/065392 A1 | 6/2011 | |
| WO | WO 2012/161040 A1 | 11/2012 | |

OTHER PUBLICATIONS

Japanese Office Action dated Aug. 25, 2015 with a partial English translation.

Japanese Office Action dated Sep. 1, 2015 with a partial English translation.

Japanese Office Action dated Nov. 4, 2015 with a partial English translation.

* cited by examiner

ULTRASOUND DIAGNOSTIC APPARATUS

BACKGROUND OF THE INVENTION

The present invention relates to an ultrasound diagnostic apparatus and a method of producing an ultrasound image. The invention more particularly relates to an ultrasound diagnostic apparatus which produces an ultrasound image based on reception signals obtained by transmission and reception of ultrasonic waves from and in an ultrasound probe and displays the produced ultrasound image on a monitor.

Heretofore, ultrasound diagnostic apparatuses that use ultrasound images have been put to practical use in the medical field. Generally in this type of ultrasound diagnostic apparatuses, a transducer array of an ultrasound probe transmits ultrasonic beams toward the inside of a subject and receives ultrasonic echoes from the subject, and a diagnostic apparatus body electrically processes reception signals to produce an ultrasound image.

An ultrasound diagnostic apparatus has recently been developed which performs various examinations based on ultrasound images and assists in the examinations themselves so that even an operator who lacks experience and knowledge can perform the examinations. For example, JP 2010-115478 A discloses an image diagnostic apparatus which aims at improving the examination efficiency and displays an examination procedure on the monitor. JP 2005-270424 A and JP 2011-10689 A disclose ultrasound diagnostic apparatuses in which an examination procedure (operation procedure) is registered in advance and an examination can be performed according to the registered examination procedure.

With such ultrasound diagnostic apparatuses, even an operator who lacks experience and knowledge can perform efficient examinations without being confused by the operation.

SUMMARY OF THE INVENTION

However, in cases where a produced ultrasound image is used to perform a preset series of examinations with a conventional ultrasound diagnostic apparatus, for example as shown in FIG. 9, all the blocks representing various examination items capable of examinations, examination sites, an execution key, and the like are displayed on an operation display screen irrespective of whether or not the examinations are to be performed, and blocks corresponding to an examination being performed are only highlighted. Although one can know the examination being performed by checking the highlighted blocks, it was not possible to understand from the operation display screen to what extent a series of examinations are performed or how many examination items still wait for examinations.

An object of the invention is to provide an ultrasound diagnostic apparatus capable of easily confirming, when an ultrasound image is used to perform a series of examinations, to what extent the examinations are performed.

In order to achieve the above object, the invention provides an ultrasound diagnostic apparatus which transmits ultrasonic waves from an ultrasound probe toward a subject, produces an ultrasound image in a diagnostic apparatus body based on reception data obtained and performs an examination based on the ultrasound image, the ultrasound diagnostic apparatus comprising: a monitor simultaneously displaying a series of examination items on an ultrasound diagnosis within a screen in chronological order; and a controller causing the monitor to highlight an examination item included in the series of examination items and being currently performed.

Preferably, the ultrasound diagnostic apparatus further comprises a selector for allowing an operator to select an examination item from among the series of examination items displayed on the monitor and, in response to a selection of the examination item through the selector, the controller controls the diagnostic apparatus body such that the examination item selected from among the series of examination items and its subsequent one or more examination items are executed.

The controller can control the diagnostic apparatus body such that the series of examination items are started from the examination item selected through the selector. In response to a selection of a subsequent examination item through the selector with one or more preceding examination items still remaining unexecuted, the controller preferably controls the diagnostic apparatus body such that the one or more preceding examination items still remaining unexecuted are skipped to execute the subsequent examination item.

In response to a selection of an already executed examination item through the selector, the controller can also control the diagnostic apparatus body such that the already executed examination item selected from among the series of examination items and its subsequent one or more examination items are executed.

The controller may cause the monitor to display a number of preformed examinations or a state of reflection of examination information together with the examination item.

Preferably, the monitor and the selector each comprise a touch panel.

According to the invention, the monitor simultaneously displays a series of examination items on the ultrasound diagnosis within a screen in chronological order and the controller highlights a currently executed examination item included in the series of examination items. Accordingly, it can be easily confirmed to what extent a series of examinations are performed.

DETAILED DESCRIPTION OF THE INVENTION

Embodiments of the invention will be described below based on the accompanying drawings.

Embodiment 1

Figure 1:
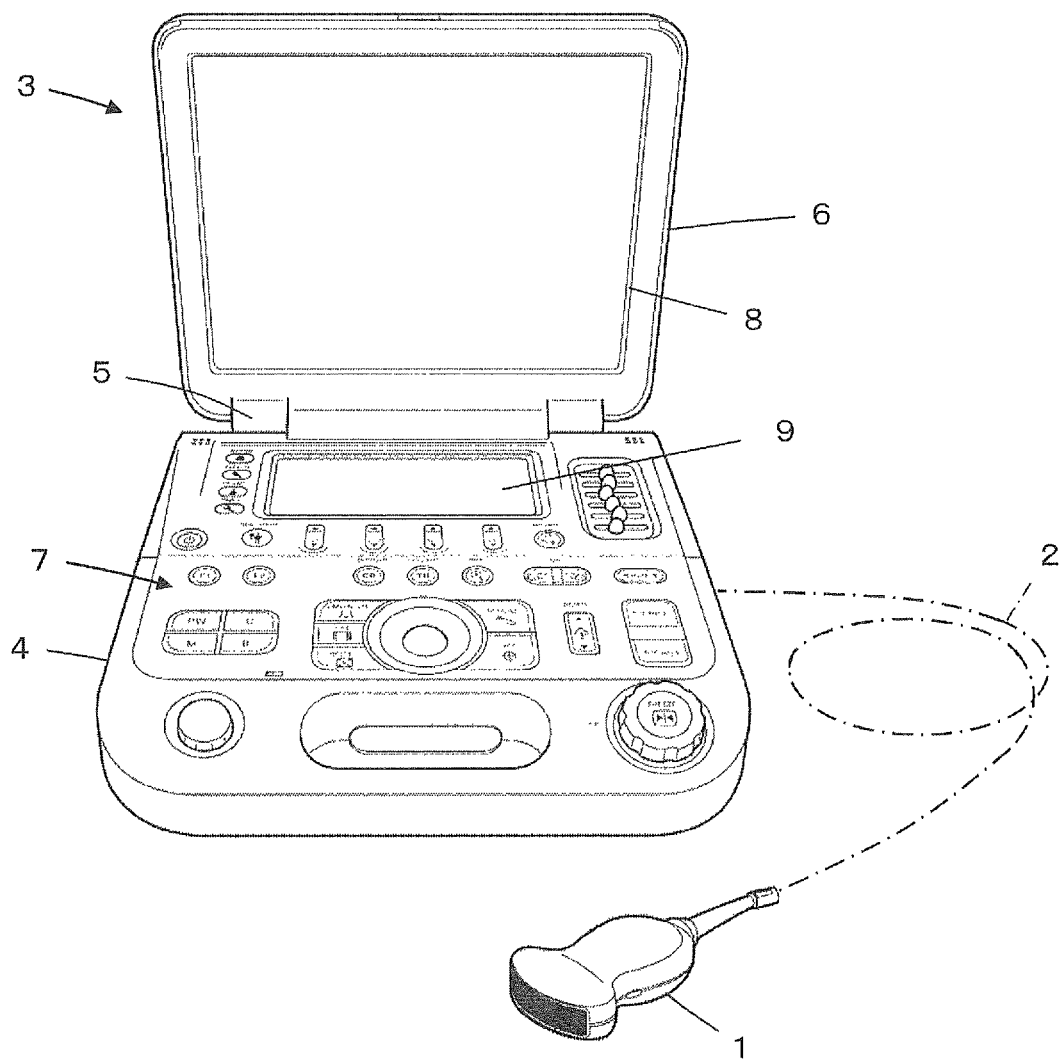
FIG. 1 is a perspective view showing an ultrasound diagnostic apparatus according to Embodiment 1 of the invention.

FIG. 1 shows an ultrasound diagnostic apparatus according to Embodiment 1 of the invention. The ultrasound diagnostic apparatus includes an ultrasound probe 1, and a diagnostic apparatus body 3 which is connected to the ultrasound probe 1 via a communication cable 2.

The diagnostic apparatus body 3 includes a housing 4 and a cover 6 rotatably attached to one end of the housing 4 via hinge portions 5. The housing 4 is substantially in the shape of a flat plate and has an operating unit 7 formed on its surface to enable an operator to perform various operations. A touch panel 9 is provided on the side of the operating unit 7 closer to the hinge portions 5. The cover 6 is also substantially in the shape of a flat plate and has an image monitor 8 formed on the internal surface of the cover 6 which is opposed to the operating unit 7 of the housing 4 by rotating it about the hinge portions 5.

Figure 2:
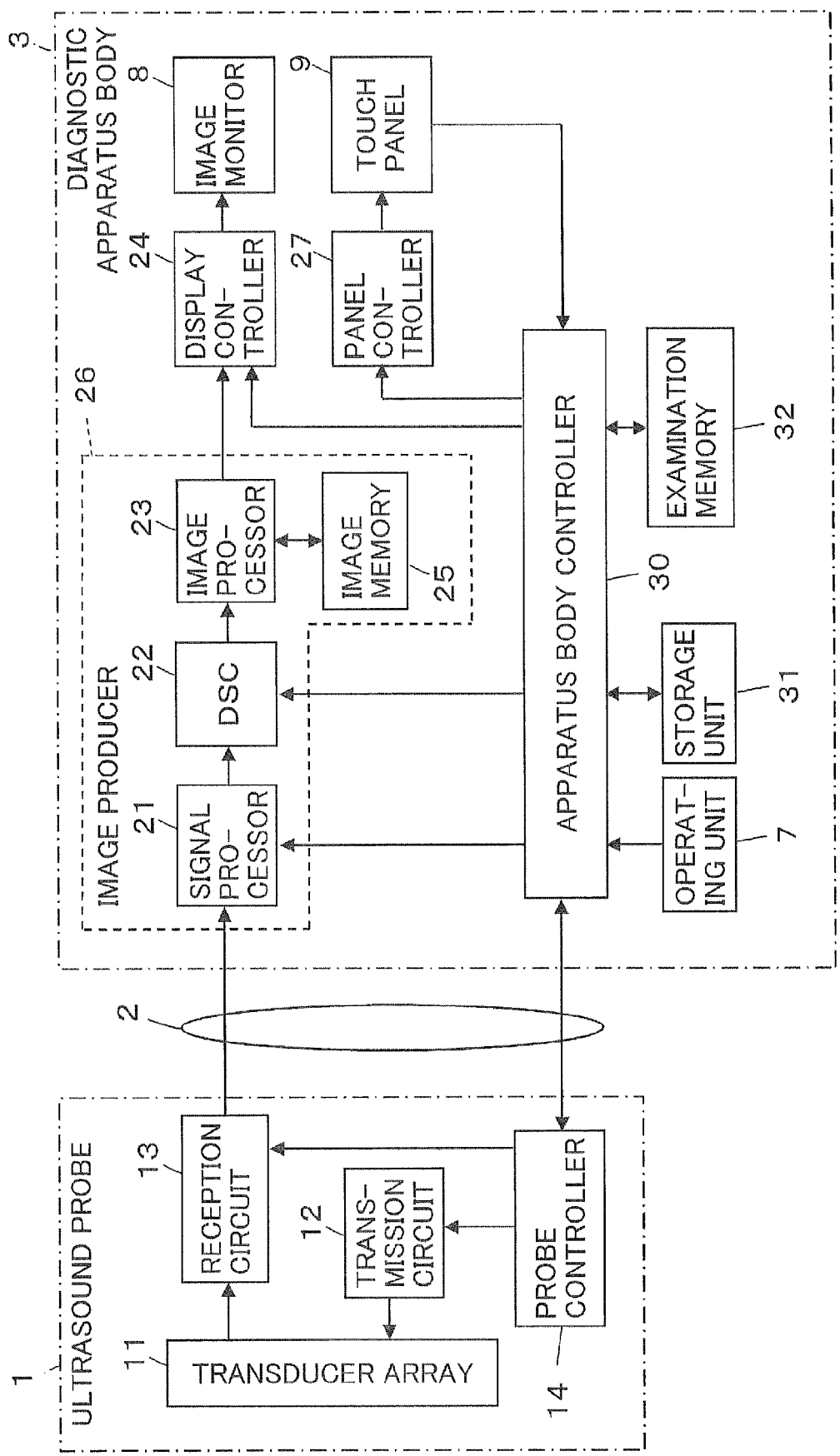
FIG. 2 is a block diagram showing the internal configuration of the ultrasound diagnostic apparatus according to Embodiment 1.

The internal configurations of the ultrasound probe 1 and the diagnostic apparatus body 3 are shown in FIG. 2.

The ultrasound probe 1 has a transducer array 11, which is connected to a transmission circuit 12 and a reception circuit 13, which in turn are connected to a probe controller 14.

The diagnostic apparatus body 3 includes a signal processor 21 connected to the reception circuit 13 of the ultrasound probe 1 via the communication cable 2; the signal processor 21 is connected in sequence to a DSC (Digital Scan Converter) 22, an image processor 23, a display controller 24, and the image monitor 8. The image processor 23 is connected to an image memory 25, and the signal processor 21, the DSC 22, the image processor 23 and the image memory 25 constitute an image producer 26. A panel controller 27 is connected to the touch panel 9.

In addition, the signal processor 21, the DSC 22, the display controller 24 and the panel controller 27 are connected to an apparatus body controller 30, which in turn is connected to the operating unit 7, a storage unit 31, an examination memory 32 and the touch panel 9.

The probe controller 14 of the ultrasound probe 1 and the apparatus body controller 30 of the diagnostic apparatus body 3 are connected to each other via the communication cable 2.

The transducer array 11 of the ultrasound probe 1 includes a one-dimensional or two-dimensional array of ultrasound transducers. These ultrasound transducers each transmit ultrasonic waves to a subject according to drive signals supplied from the transmission circuit 12, receive ultrasonic echoes from the subject and output reception signals. Each of the ultrasound transducers includes a vibrator having a piezoelectric body and electrodes provided on both ends of the piezoelectric body, and the piezoelectric body is made of, for example, a piezoelectric ceramic material typified by PZT (lead zirconate titanate), a piezoelectric polymer typified by PVDF (polyvinylidene fluoride) or a piezoelectric single crystal typified by PMN-PT (lead magnesium niobate-lead titanate solid solution).

When a pulsed voltage or a continuous-wave voltage is applied to the electrodes of such a vibrator, the piezoelectric body expands and contracts to cause the vibrator to generate pulsed or continuous ultrasonic waves and these ultrasonic waves are combined to form an ultrasonic beam. Upon reception of propagating ultrasonic waves, the vibrator expands and contracts to produce electric signals, which are then outputted as signals of the received ultrasonic waves.

The transmission circuit 12 includes, for example, a plurality of pulsers and adjusts the delay amounts of drive signals based on a transmission delay pattern selected according to a control signal from the probe controller 14 so that the ultrasonic waves transmitted from the ultrasound transducers of the transducer array 11 form an ultrasonic beam, and supplies the ultrasound transducers with adjusted drive signals.

The reception circuit 13 subjects the reception signals transmitted from the ultrasound transducers of the transducer array 11 to amplification and A/D conversion, and then performs reception focusing processing by providing the reception signals with respective delays according to the sonic speed or sonic speed distribution that is set based on a reception delay pattern selected according to the control signal from the probe controller 14 and adding them up. This reception focusing processing yields reception data (sound ray signals) where the ultrasonic echoes are well focused.

The probe controller 14 controls the respective components of the ultrasound probe 1 based on various control signals transmitted from the apparatus body controller 30 of the diagnostic apparatus body 3.

The signal processor 21 of the diagnostic apparatus body 3 corrects the attenuation in the reception data produced by the reception circuit 13 of the ultrasound probe 1 according to the distance, i.e., the depth at which the ultrasonic waves are reflected, and then performs envelope detection processing to produce a B mode image signal, which is tomographic image information on a tissue inside the subject's body.

The DSC 22 converts the B mode image signal produced in the signal processor 21 into an image signal compatible with an ordinary television signal scanning mode (raster conversion).

The image processor 23 performs various necessary image processing including gradation processing on the B mode image signal entered from the DSC 22 before outputting the B mode image signal to the display controller 24 or storing the B mode image signal in the image memory 25.

The display controller 24 causes the image monitor 8 to display an ultrasound diagnostic image based on the B mode image signal having undergone image processing in the image processor 23.

The image monitor 8 includes a display device such as an LCD, for example, and displays an ultrasound diagnostic image under the control of the display controller 24. At the time of examination, examination tools such as a cursor and calipers are displayed as required in a superimposed manner on an ultrasound diagnostic image.

The operating unit 7 is disposed on the surface of the housing 4 and has various operating buttons with which an operator performs input operations.

The storage unit 31 stores, for example, operation programs and examination programs including a series of examination items and recording media such as a hard disk, a flexible disk, an MO, an MT, a RAM, a CD-ROM, a DVD-ROM, an SD card, a CF card, and a USB memory, and a server may be used.

The examination memory 32 is a memory in which information on the examination results including measured values obtained by the examinations is stored.

The apparatus body controller 30 controls the respective components in the diagnostic apparatus body 3 based on various instruction signals entered by the operator using the operating unit 7.

The signal processor 21, the DSC 22, the image processor 23, the display controller 24, and the panel controller 27 are each constituted by a CPU and an operation program for causing the CPU to perform various kinds of processing, but they may be each constituted by a digital circuit.

The panel controller 27 causes the touch panel 9 to display an operation display image corresponding to the series of examination items outputted from the apparatus body controller 30.

The touch panel 9 is a device including the display function and the position input function in combination, and a transparent membrane sensor for detecting that an operator touched the display device such as an LCD is attached to the touch panel 9 so that a predetermined operation signal is outputted based on the representation on the display and the position on the membrane sensor at which the operator touched the membrane sensor. Detection systems such as resistive system and capacitive system may be used in the membrane sensor.

The operation entered using the touch panel 9 is outputted to the apparatus body controller 30 as an operation signal to cause the apparatus body controller 30 to perform a specified operation.

The touch panel 9 may be replaced by an operation monitor and an operation selector.

Next, the operation of Embodiment 1 will be described.

Pressing a power switch provided in the operating unit 7 of the housing 4 in the diagnostic apparatus body 3 causes electric power to be supplied to the respective components in the diagnostic apparatus body 3 and the ultrasound probe 1 to start the ultrasound diagnostic apparatus.

The ultrasound transducers of the transducer array 11 sequentially transmit ultrasonic beams according to the drive signals from the transmission circuit 12 of the ultrasound probe 1, and the reception signals received by the respective ultrasound transducers are sequentially outputted to the reception circuit 13, where reception data is produced. The image producer 26 of the diagnostic apparatus body 3 produces image signals based on the reception data and the display controller 24 causes the image monitor 8 to display an ultrasound image based on the image signals.

Next, a desired examination is performed based on the ultrasound image produced and displayed on the image monitor 8.

Figure 3:
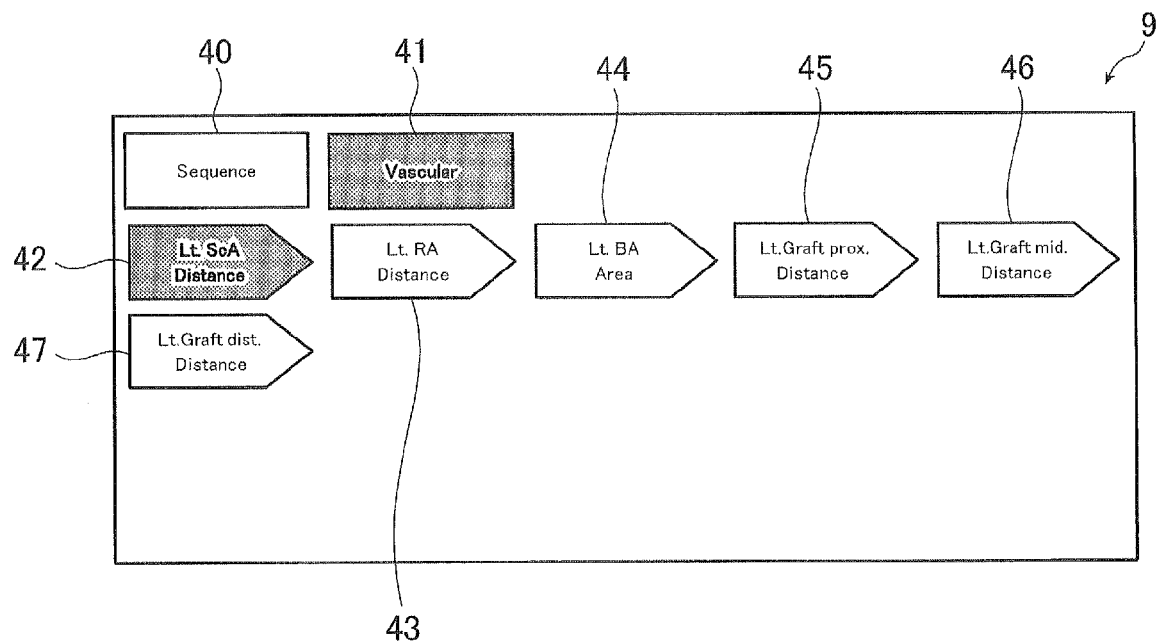
FIG. 3 is a diagram showing an example of the operation display in performing a series of vascular examinations in Embodiment 1.

For example, a series of examination items for performing a series of examinations as shown in FIG. 3 are simultaneously displayed in blocks within a screen in chronological order on the touch panel 9 of the housing 4. The series of examination items are preset in a plurality of examination programs stored in the storage unit 31 and one examination program can also be displayed by being invoked from the storage unit 31 through the operating unit 7 and the apparatus body controller 30. Alternatively, the operating unit 7 or the touch panel 9 may be operated to prepare a new series of examination items.

Highlighted blocks 41 and 42 in FIG. 3 indicate examination items for which an examination is currently performed.

Sequence block 40 in FIG. 3 indicates that a series of examination items are currently displayed in sequence on the touch panel 9. The highlighted Vascular block 41 indicates that a vascular examination is currently performed on an ultrasound image.

Blocks 42 to 47 arranged in chronological order indicate a series of vascular examination items.

Lt. ScA Distance block 42 indicates an examination item for measuring the distance of the left subclavian artery; Lt. RA Distance block 43 an examination item for measuring the distance of the left radial artery; Lt. BA Area block 44 an examination item for measuring the area of the left brachial artery; and Lt. Graft prox. Distance block 45, Lt. Graft mid. Distance block 46 and Lt. Graft dist. Distance block 47 examination items for measuring the distances of the left arterial graft, respectively.

In FIG. 3, the Lt. ScA Distance block 42 is currently highlighted, which shows that, of the series of examination items simultaneously displayed within a screen in chronological order, the examination for measuring the distance of the left subclavian artery is performed.

In this case, for example, the apparatus body controller 30 causes, through the display controller 24, the image monitor 8 to display a caliper for measuring the left subclavian artery in a superimposed manner on the ultrasound image; and the operator manipulates the operating unit 7 to operate the caliper to thereby measure the distance of the left subclavian artery seen on the ultrasound image. The apparatus body controller 30 measures the distance, for example, based on two positions determined by the caliper.

Upon measurement of the distance of the left subclavian artery, the apparatus body controller 30 causes the examination memory 32 to store distance information of the left subclavian artery and also causes, through the display controller 24, the image monitor 8 to display the distance information. Upon completion of the measurement of the distance of the left subclavian artery, the apparatus body controller 30 returns the Lt. ScA Distance block 42 to normal display and highlights the Lt. RA Distance block 43 which indicates the next examination item.

The apparatus body controller 30 causes, through the display controller 24, the image monitor 8 to display a caliper for measuring the distance of the left radial artery in a superimposed manner on the ultrasound image. This operation and its subsequent operations are the same as those in the case of measuring the distance of the left subclavian artery.

When the subsequent operations are performed in the same manner to complete the examinations for all the series of examination items in the blocks 42 to 47 displayed on the touch panel 9 and store information based on the examinations in the examination memory 32, the series of examinations based on the ultrasound image are finished.

In Embodiment 1, the series of examination items are simultaneously displayed within a screen in chronological order and examination items for which an examination is currently performed are highlighted. Therefore, the operator can know at first sight to what extent the series of examinations are performed and the series of examinations can be performed with high efficiency.

Embodiment 2

Next, the operation of the ultrasound diagnostic apparatus according to Embodiment 2 of the invention which is capable of changing the start position of a series of examinations will be described by illustrating a series of examinations commonly used in obstetrics. The configuration of the ultrasound diagnostic apparatus according to Embodiment 2 is the same as that of the apparatus according to Embodiment 1 shown in FIGS. 1 and 2.

Figure 4:
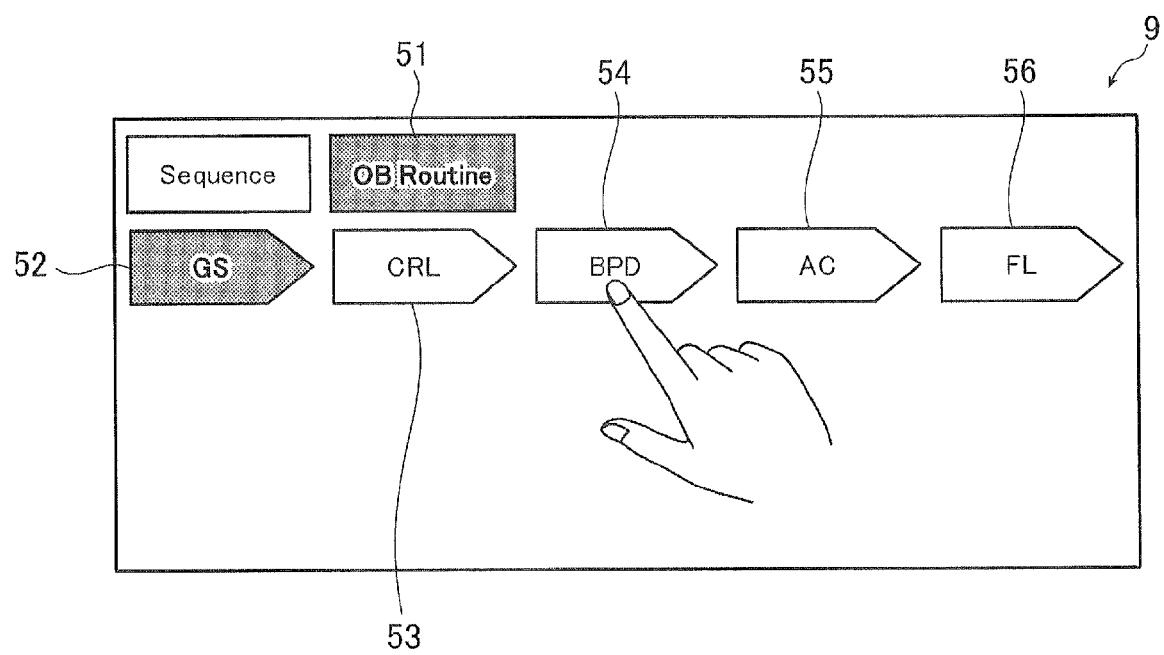
FIG. 4 is a diagram showing an example of the operation display in performing a series of obstetric examinations in Embodiment 2.

FIG. 4 shows an example of the operation display of the touch panel 9 in the case of performing the series of examinations commonly used in obstetrics. Sequence block 50 and OB Routine block 51 in FIG. 4 indicate that the series of examination items stored in advance in the ultrasound diagnostic apparatus and commonly used in obstetrics are currently displayed in sequence on the touch panel 9.

In FIG. 4, GS block 52 indicates an examination item for checking the gestational sac; CRL block 53 an examination item for measuring the crown rump length; BPD block 54 an examination item for measuring the biparietal diameter; AC block 55 an examination item for measuring the abdominal circumference; and FL block 56 an examination item for measuring the femur length.

Of the series of examination items shown in FIG. 4, the highlighted first GS block 52 indicates the default start position and the series of examinations are usually started from the examination for checking the gestational sac in the GS block 52.

Of the series of examination items GS, CRL, BPD, AC and FL commonly used in obstetrics, subjects in the first trimester of pregnancy are examined only for the examination items GS, CRL and BPD and subjects in the second trimester of pregnancy are examined only for the examination items BPD, AC and FL.

Therefore, according to Embodiment 2, the start position of the series of examinations can be changed depending on the pregnancy stage of subjects.

Figure 5:
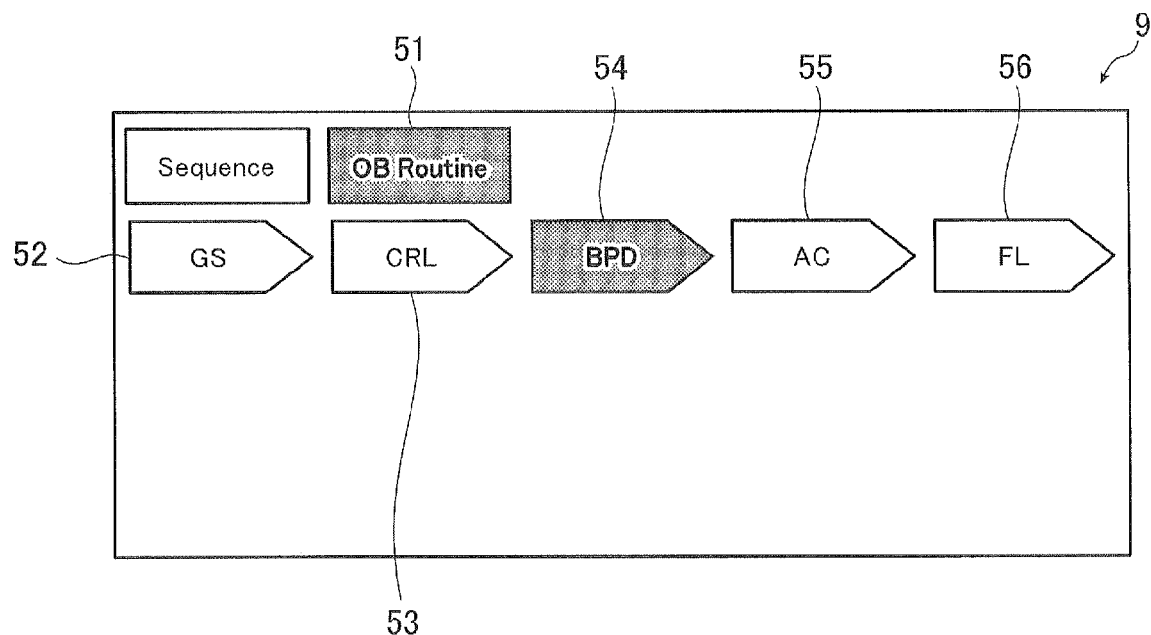
FIG. 5 is a diagram showing the operation display in selecting a specified examination item in FIG. 4.

In the case of a subject in the second trimester of pregnancy, of the series of examination blocks displayed on the touch panel 9, the operator touches the BPD block 54 to select the examination item BPD as shown in FIG. 4, thereby changing the examination start position to the examination item BPD as shown in FIG. 5. More specifically, the apparatus body controller 30 receives an operation signal from the touch panel 9 and highlights the BPD block 54 of the touch panel 9 through the panel controller 27.

Upon change of the start position to the BPD block 54, the apparatus body controller 30 controls the display controller 24 and the image monitor 8 as above to display a caliper or the like necessary for the measurement on the ultrasound image in a superimposed manner.

Although not shown, a subject in the first trimester of pregnancy undergoes examinations in the examination items GS and CRL before ending with the examination in the examination item BPD. An instruction for the examination end is issued through the operating unit 7 or the touch panel 9 after the measurement is performed.

In Embodiment 2, the examination start position can be thus changed in the series of examinations to avoid unnecessary examinations, thereby reducing the burden on subjects while increasing the examination efficiency.

Of the series of examination items, the above-described default start position can also be changed in advance. For example, the default start position may be changed in advance from the GS block 52 to the BPD block 54 to mainly examine subjects in the second and third trimesters of pregnancy.

Embodiment 3

Next, the operation of the ultrasound diagnostic apparatus according to Embodiment 3 of the invention which is capable of skipping a specified examination will be described by illustrating a series of examinations for measuring the amount of amniotic fluid. The configuration of the ultrasound diagnostic apparatus according to Embodiment 3 is also the same as that of the apparatus according to Embodiment 1 shown in FIGS. 1 and 2.

Figure 6A:
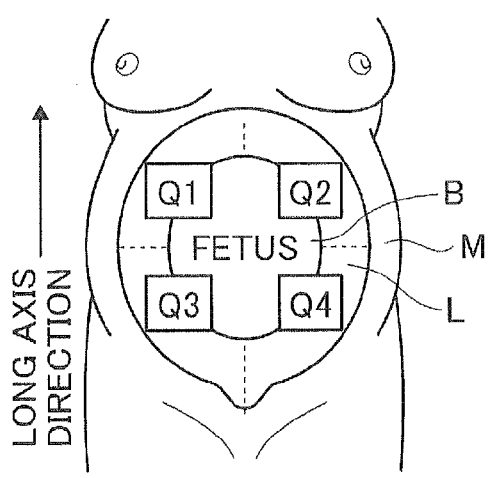
FIG. 6A is a diagram schematically showing the positional relationship between a mother's body and a fetus in the case where the fetus is not deviated in position.

As shown in FIG. 6A, when a fetus B is positioned near the center of a mother's body M, the amount of amniotic fluid L is calculated by measuring the depths of the free spaces in areas Q1 to Q4 shown in FIG. 6A and summing them up.

Figure 6B:
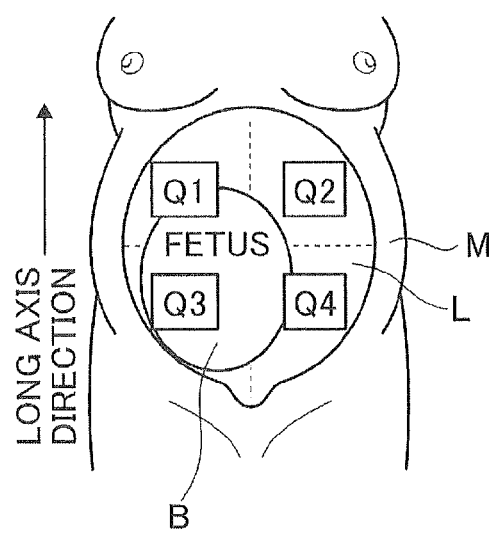
FIG. 6B is a diagram schematically showing the positional relationship between a mother's body and a fetus in the case where the fetus is deviated in position.

However, if the fetus B is, for example, deviated in position toward the area Q3 among the areas Q1 to Q4 of the mother's body M as shown in FIG. 6B, the area Q3 has a small distance between the measurement point and the fetus and hence does not have enough depth to enable the measurement to be performed. Therefore the measurement in the area Q3 is not necessary.

FIGS. 7A to 7D show examples of the operation display of the touch panel 9 in the case of the examination for measuring the amount of amniotic fluid. In FIGS. 7A to 7D, AFI block 61 indicates the examination of the amniotic fluid index, and a series of blocks including Q1 block 62 to Q4 block 65 indicate examination items corresponding to the positions of the areas Q1 to Q4 in the mother's body M shown in FIGS. 6A and 6B.

Figure 7A:
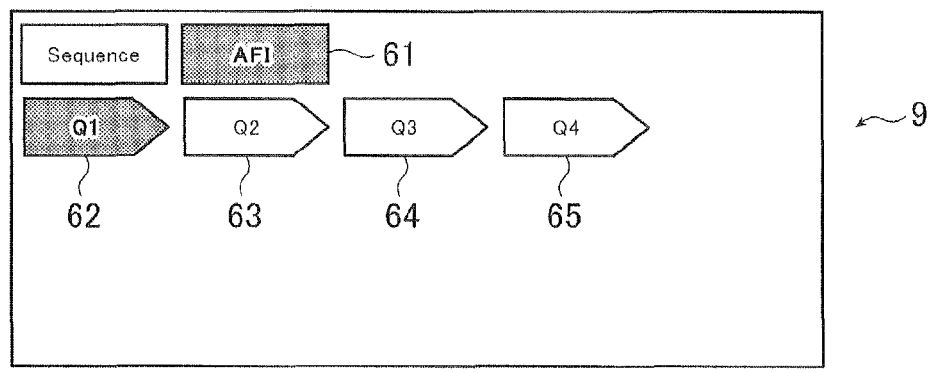
FIGS. 7A to 7D are diagrams showing step by step the operation display in checking the amount of amniotic fluid in Embodiment 3.
Figure 7B:
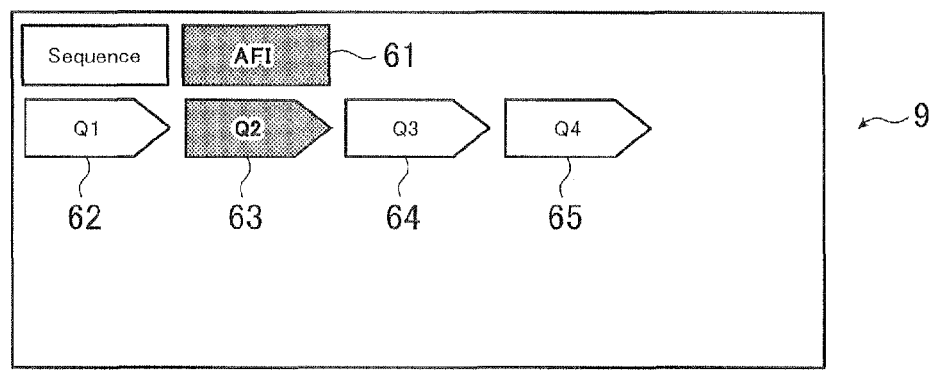
Figure 7C:
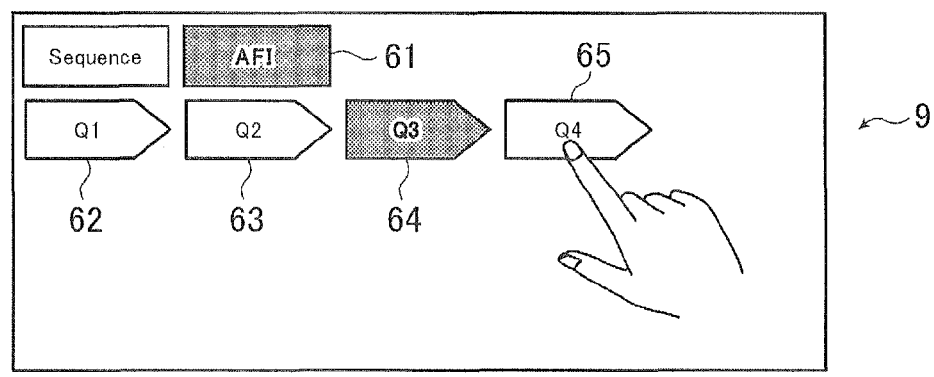
Figure 7D:
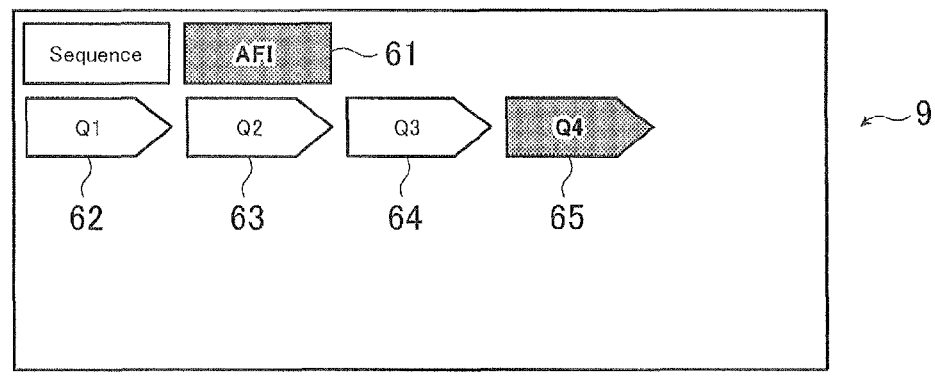

If it is known that the fetus is deviated toward the area Q3, the examinations in the examination items Q1 and Q2 are performed as shown in FIGS. 7A and 7B, and when the Q3 block 64 indicating the next examination item is highlighted as shown in FIG. 7C, the operator touches the Q4 block 65 of the touch panel 9 to select the examination item Q4, thereby enabling the unnecessary examination item Q3 to be skipped to transfer to the subsequent examination item Q4 as shown in FIG. 7D. More specifically, the apparatus body controller 30 receives an operation signal from the touch panel 9 and highlights the Q4 block 65 of the touch panel 9 through the panel controller 27. Of course, it is also possible to skip a plurality of examination items.

In Embodiment 3, by thus merely selecting any of subsequent examination blocks which are not highlighted on the touch panel 9, an unnecessary examination in the series of examinations can be skipped very easily to reduce the burden on subjects (the fetus and the mother in this embodiment) while increasing the examination efficiency.

Embodiment 4

In cases where the body weight of a fetus is calculated in any of the ultrasound diagnostic apparatuses in Embodiments 1 to 3, the body weight is estimated using measured values of the above-described BPD (biparietal diameter), AC (abdominal circumference) and FL (femur length) but as for the measurement accuracy on the ultrasound image, the values greatly change due to some operation and are therefore to be determined in some cases after the whole is once checked.

Figure 8A:
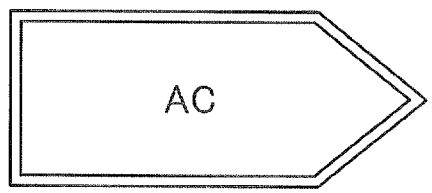
FIG. 8A is a diagram showing one block in the operation display in Embodiment 4, examination information being reflected in the examination item of this block.

In such a case, whether the body weight value is a value before or after the reflection of the measured values (examination information) obtained by the examinations is preferably recognizable on the touch panel 9. In this case, whether the body weight value is a value before or after the reflection of the examination information may be recognizable by highlighting the shape of the examination block as shown in FIG. 8A.

Some examination programs execute the same examination a plurality of times and use the average of measured values.

Figure 8B:
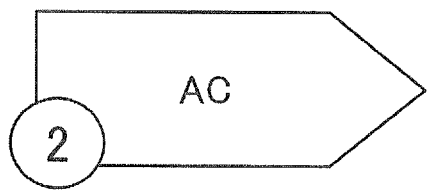
FIG. 8B is a diagram showing a block of an examination item for which the number of the already performed examinations is reflected.
Figure 9:
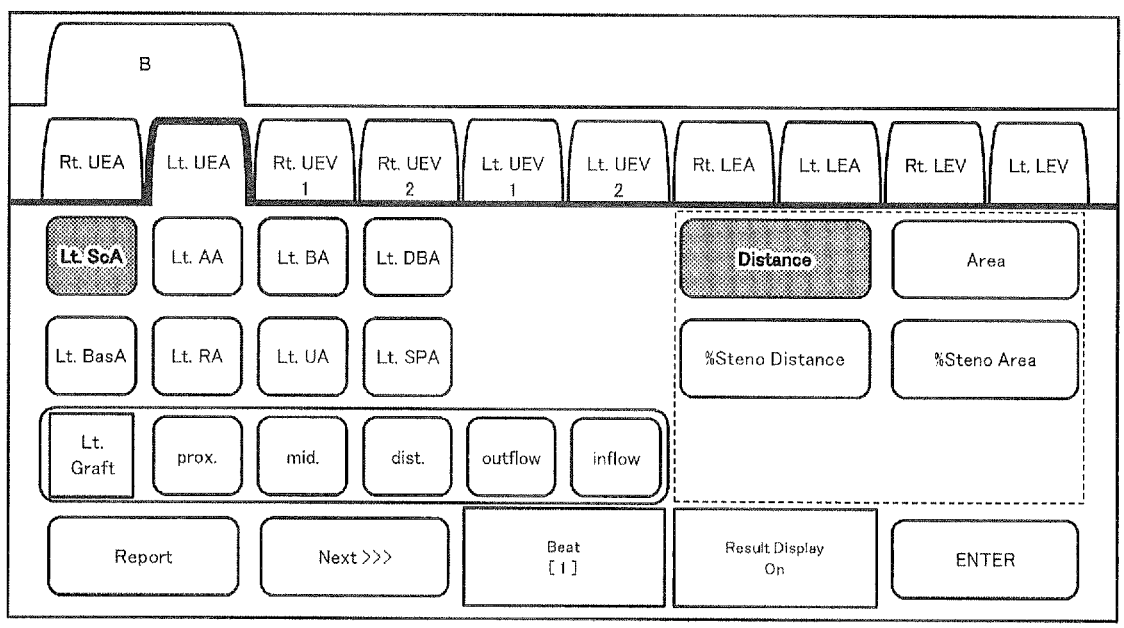
FIG. 9 is a diagram showing the operation display in a conventional ultrasound diagnostic apparatus.

In such a case, the series of examinations can be preferably recognized on the touch panel 9 as to whether the first measurement or the second measurement is performed. In this case, the ultrasound diagnostic apparatus can be configured so that the number of examinations can be known, for example, by displaying the number of examinations on the examination block in a superimposed manner, as shown in FIG. 8B.

The ultrasound diagnostic apparatus may also be configured so that the operator selects an already executed examination block included in the series of examination blocks displayed on the touch panel to return to the already executed examination item and execute this examination item and its subsequent series of examination items again. Also in this case, as described above, the number of examinations is preferably displayed on the examination block for which the examination was performed a plurality of times.

While the ultrasound diagnostic apparatus of the invention has been described above in detail, the invention is by no means limited to the above embodiments, and various improvements and modifications may be made without departing from the scope and spirit of the invention.

What is claimed is:

1. An ultrasound diagnostic apparatus which transmits ultrasonic waves from an ultrasound probe toward a subject, produces an ultrasound image in a diagnostic apparatus body based on reception data obtained and performs an examination based on said ultrasound image, the ultrasound diagnostic apparatus comprising:

an operation monitor simultaneously displaying in blocks a name of said desired examination and a series of examination items that can be performed in said desired examination within a screen, said series of examination items being arranged in chronological order according to a procedure; and a controller causing said operation monitor to highlight a block of an examination item included in said series of examination items and being currently performed, wherein said series of examination items is any one selected from a series of vascular examinations, a series of obstetric examinations, a series of examinations for measuring amount of amniotic fluid and a series of examinations for measuring a body weight of fetus, and wherein said controller causes said operation monitor to display a number of performed examinations.

2. The ultrasound diagnostic apparatus according to claim 1, further comprising an operation selector for allowing an operator to select an examination item from among said series of examination items displayed in blocks on said operation monitor, wherein, in response to a selection of the examination item through said operation selector, said controller controls said diagnostic apparatus body such that the examination item selected from among said series of examination items and its subsequent one or more examination items are executed.

3. The ultrasound diagnostic apparatus according to claim 2, wherein said controller controls said diagnostic apparatus body such that said series of examination items are started from the examination item selected through said operation selector.

4. The ultrasound diagnostic apparatus according to claim 2, wherein, in response to a selection of a subsequent examination item through said operation selector with one or more preceding examination items still remaining unexecuted, said controller controls said diagnostic apparatus body such that said one or more preceding examination items still remaining unexecuted are skipped to execute said subsequent examination item.

5. The ultrasound diagnostic apparatus according to claim 2, wherein, in response to a selection of an already executed examination item through said operation selector, said controller controls said diagnostic apparatus body such that said already executed examination item selected from among said series of examination items and its subsequent one or more examination items are executed.

6. The ultrasound diagnostic apparatus according to claim 2, wherein said operation monitor and said operation selector each comprise a touch panel.

7. The ultrasound diagnostic apparatus according to claim 1, further comprising an operation selector for allowing an operator to select an examination item as a start position of the series from among said series of examination items displayed in blocks on said operation monitor.

8. The ultrasound diagnostic apparatus according to claim 1, further comprising an operation selector for allowing an operator to input a default start position as an examination item from among said series of examination items displayed in blocks on said operation monitor.

9. The ultrasound diagnostic apparatus according to claim 1, further comprising an operation selector for allowing an operator to select an examination item to be skipped from among said series of examination items displayed in blocks on said operation monitor.

10. The ultrasound diagnostic apparatus according to claim 1, further comprising an operation selector for allowing an operator to select a plurality of examination items to be skipped from among said series of examination items displayed in blocks on said operation monitor.

* * * * *